United States Patent [19]

Manzer et al.

[11] Patent Number: 5,177,224

[45] Date of Patent: Jan. 5, 1993

[54] PROCESS FOR THE PREPARATION OF HALOGENATED 2,2-BIS(TRIFLUOROMETHYL)-1,3-DIOXOLANES

[75] Inventors: Leo E. Manzer; Paul R. Resnick, both of Wilmington, Del.

[73] Assignee: E. I. Du Pont de Nemours and Company, Wilmington, Del.

[21] Appl. No.: 759,095

[22] Filed: Sep. 6, 1991

Related U.S. Application Data

[63] Continuation of Ser. No. 399,100, Aug. 28, 1989, abandoned.

[51] Int. Cl.⁵ .......................................... C07D 317/16
[52] U.S. Cl. .................................................. 549/455
[58] Field of Search ................. 549/455; 570/170, 254

[56]   References Cited

U.S. PATENT DOCUMENTS

| | | | |
|---|---|---|---|
| 2,498,552 | 2/1950 | Kilgren et al. ............. | 570/254 |
| 3,749,791 | 7/1973 | Terreli et al. ............. | 549/455 |
| 3,865,845 | 2/1975 | Resnick .................... | 549/455 |
| 4,053,530 | 10/1977 | Schindel ................... | 570/170 |
| 4,496,750 | 1/1985 | Anderson et al. ............ | 549/455 |
| 4,535,175 | 8/1985 | Squire ..................... | 549/455 |

FOREIGN PATENT DOCUMENTS

| | | | |
|---|---|---|---|
| 0317981 | 5/1989 | European Pat. Off. . | |
| 511861 | 2/1939 | United Kingdom ............. | 549/455 |
| 1361346 | 7/1974 | United Kingdom . | |

OTHER PUBLICATIONS

Roberts et al., "Basic Principles of Organic Chemistry", W. A. Benjamin, Inc., New York, 1965, pp. 315–318.
J. Fluorine Chem., vol. 9, No. 9, 1977, R. D. Bagnall et al.: "New Inhalation Anaesthetics:I. Fluorinated 1,3-Dioxolane Derivatives", pp. 359–375, see p. 371.

*Primary Examiner*—Nicky Chan
*Attorney, Agent, or Firm*—R. Thomas Gallegos

[57]   ABSTRACT

A process for the production of a halogenated 2,2-bis(trihaloalkyl)-1,3-dioxolane of the formula

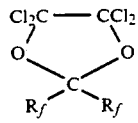

wherein $R_f$ is perhaloalkyl comprising a 2,2-bis(trihaloalkyl)-1,3-dioxolane in the presence of at least one of La, Ni, Sn, Zn, Fe, Co or Cu is disclosed.

A process for the production of a halogenated 2,2-bis(trihaloalkyl)-1,3-dioxolane of the formula

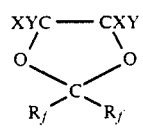

wherein X is Cl and each Y is independently Cl or F and wherein at least one Y is F, comprising fluorinating a halogenated 2,2-bis(trifluoromethyl)-4,4,5,5-tetrachloro-1,3-dioxolane in the presence of a catalyst which is preferably $Cr_2O_3$ is disclosed.

A process for the production of a 2,2-bis(trihaloalkyl)-1,3-dioxole of the formula

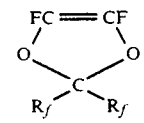

comprising dehalogenating substantially only a corresponding trans-2,2-bis(perhaloalkyl)-4,5-difluoro-4,5-dichloro-1,3-dioxolane is disclosed.

14 Claims, No Drawings

PROCESS FOR THE PREPARATION OF HALOGENATED 2,2-BIS(TRIFLUOROMETHYL)-1,3-DIOXOLANES

This application is a continuation of Ser. No. 399,100, filed Aug. 28, 1989 now abandoned.

BACKGROUND OF THE INVENTION

The invention concerns a catalytic process for the preparation of halogenated 2,2-bis(trifluoromethyl)-1,3-dioxolanes.

2,2-Bis(trifluoromethyl)-1,3-dioxolane is a known compound which may be halogenated according to a number of known methods to produce various halo-isomers at the 4,5 or 4 and 5 positions. For example, U.S. Pat. No. 2,925,424 describes a batch photochemical chlorination of 2,2-bis(trifluoromethyl)-1,3-dioxolane. The reaction was conducted at 50° C. for 2.5 hours. A 68% yield of 2,2-bis(trifluoromethyl)-4,4,5,5-tetrachloro-1,3-dioxolane was obtained upon fractionation of crude product. See Example 9.

U.S. Pat. No. 4,535,175 discloses a batch photochemical chlorination of 2,2-bis(trifluoromethyl)-1,3-dioxolane to yield a mixture of di-, tri- and tetrachloro derivatives. The reaction proceeds rather slowly. Example 1 of the patent details the production of 2,2-bis(trifluoromethyl)-4,4,5-trichloro-5-fluoro-1,3-dioxolane by reacting 2,2-bis(trifluoromethyl)-4,4,5,5,-tetrachloro-1,3-dioxolane, HF and antimony chloride at 70° C. for 5 hours.

U.S. Pat. No. 3,749,791 discloses a batch photochlorination of 2,2-bis(trifluoromethyl)-1,3-dioxolane at −15° C. Example 1 describes the synthesis of 2,2-bis(trifluoromethyl)-4-chloro-1,3-dioxolane. Example 2 of the patent describes the synthesis of 2,2-bis(trifluoromethyl)-4,5-dichloro-1,3-dioxolane.

G.B. 1,361,346 discloses the preparation of 2,2-bis(trifluoromethyl)-4,5-dichloro-4,5-difluoro-1,3-dioxolane by fluorinating 2,2-bis(trifluoromethyl)-4,4,5,5,-tetrachloro-1,3-dioxolane with $SbF_3/SbCl_5$ at 120° C.

SUMMARY OF THE INVENTION

The invention provides a process for the preparation of 2,2-bis(perhaloalkyl)-4,4,5,5-tetrachloro-1,3-dioxolane by chlorinating 2,2-bis(perhaloalkyl)-1,3-dioxolane with a source of chlorine in the presence of a catalyst which contains at least one of La, Ni, Sn, Zn Co, Fe, or Cu.

The invention also provides a process for the preparation of fluorinated 2,2-bis(perhaloalkyl)-1,3-dioxolanes of the formula

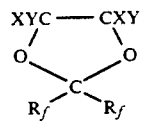

wherein X is Cl, each Y is independently Cl or F and at least one Y is F and each $R_f$ is independently perhaloalkyl in which the alpha carbon is substituted by at least one fluorine atom.

The process comprises fluorinating 2,2-bis(perhaloalkyl)-4,4,5,5-tetrachloro-1,3-dioxolane with a source of fluorine under fluorination conditions, so as to effect fluorine-chlorine exchange, in the presence of a catalyst which is a catalyst as noted above in the chlorination reaction or is chromium (III) oxide, i.e., $Cr_2O_3$ or one or more of a metal supported on carbon wherein the metals are chosen from Cr, Co, La, Fe, Ni, Cu, Sn, or Zn.

DETAILED DESCRIPTION

Preferably, $R_f$ is trifluoromethyl. The 2,2-bis(perhaloalkyl)-1,3-dioxolane starting material for the chlorination is a known compound which may be readily prepared by reacting perfluoroacetone and ethylene chlorohydrin under basic conditions as described in U.S. Pat. No. 2,925,424.

The chlorination is preferably conducted in the vapor phase, and is preferably conducted continuously. However, the reaction may be conducted in the liquid phase using the reactants as solvents, at the same temperatures noted for the vapor phase, under autogenous pressure. Preferred temperatures for the reaction are 250°–300° C. The molar ratio of chlorine to 2,2-bis(perhaloalkyl)-1,3-dioxolane is preferably about 4:1 to 10:1, more preferably about 4:1 to 5:1. The reaction time is generally about 1 to 120 seconds, and is preferably about 30 to 60 seconds. The reaction pressure is preferably about 1 to 20 atmospheres, more preferably about 10 to 20 atmospheres. The preferred source of chlorine is chlorine gas. The catalyst metal may be in the form of any soluble compound of the metal such as the oxide, oxyhalide, halide, pseudohalide, nitrate, sulfate, or organic salt such as acetate and propionate. The halides include chlorides, fluorides and bromides. The pseudohalides include cyanides, cyanates and thiocyanates. The form of the catalyst is not critical and may be pellets, powders or granules. Preferably, the catalysts are used in a fixed bed; however, fluidized bed reactors may also be used. Preferably, the catalysts are in the form of their chlorides, and preferably are supported on carbon. The preferred catalyst for the chlorination is $CuCl_2/C$.

General Procedure for Preparing Catalysts $MCl_x/C$

The desired amount of metal chloride was dissolved in water (35 to 75 mL) and the entire solution poured over 40 g of commercial carbon granules (Girdler 411, 0.32 cm pellets). The resulting mixture was allowed to stand at room temperature for one hour and was then placed in a vacuum oven at 110° C. for 16 to 24 hours to remove the water. The catalyst was then pretreated by heating in an atmosphere of nitrogen gas at 400° C. followed by heating in HF at 400° C. prior to its use as a fluorination catalyst. For chlorination reactions, the catalyst was heated in an atmosphere of nitrogen gas at 400° C. followed by adjusting the temperature to the desired value and treatment with chlorine gas. Preferably, 0.1–30% b.w. based on the support of active metal is incorporated in the catalyst.

Catalyst Preparation

The following catalysts were prepared by the general procedure for $MCl_x/C$:

| | |
|---|---|
| $CoCl_2/C$ | 35 g $CoCl_2.6H_2O$/35 mL $H_2O$ |
| $FeCl_3/C$ | 39.7 g $FeCl_3.6H_2O$/35 mL $H_2O$ |
| $ZnCl_2/C$ | 20.44 g $ZnCl_2$/75 mL $H_2O$ |
| $NiCl_2/C$ | 34.94 g $NiCl_2.6H_2O$/35 mL $H_2O$ |
| $LaCl_3/C$ | 62.43 g $LaCl_3.7H_2O$/75 mL $H_2O$ |
| $CrCl_3/C$ | 39.17 g $CrCl_3.6H_2O$/60 mL $H_2O$ |
| $SnCl_2/C$ | 38.36 g $SnCl_2.2H_2O$/70 mL $H_2O$ |
| $CuCl_2/C$ | 25.06 g $CuCl_2.2H_2O$/70 mL $H_2O$ |

Cr$_2$O$_3$ is commercially available and was treated with HF as described above prior to its use as a fluorination catalyst.

The catalysts having differing anions are prepared analogously.

The fluorination is preferably conducted in the vapor phase, and is preferably conducted continuously. The reaction may be conducted in the liquid phase as indicated for the chlorination. The reaction temperature is preferably 150° to 350° C., more preferably 150° to 200° C. The preferred source of fluorine is HF. The molar ratio of HF to 2,2-bis(perhaloalkyl)-4,4,5,5-tetrachloro-1,3-dioxolane is preferably about 2:1 to 10:1, more preferably about 2:1 to 5:1. Preferred reaction time is about 1 to 120 seconds, more preferably about 30 to 60 seconds. The preferred catalyst for the fluorination is Cr, more preferably unsupported Cr$_2$O$_3$.

The production of the fluoro-compounds may be conducted in two steps, with, e.g., isolation of a 2,2-bis(perhaloalkyl)-4,4,5,5-tetrachloro-1,3-dioxolane intermediate, or may be conducted in one enclosure with the addition of the fluorine source preferably after substantial completion of the first reaction.

The catalysts of the invention are extremely active and selective. In the fluorination, where Cr$_2$O$_3$ is the catalyst, the ratio of trans to cis isomers is desirably high.

The products of the process of the invention are useful as intermediates in the production of perhalodioxoles of the formula

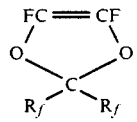

by dehalogenation of the appropriate precursor according to conventional processes, for example, as disclosed in U.S. Pat. Nos. 4,535,175, 3,865,845, and 3,978,030.

Preferably, trans-2,2-bis(perhaloalkyl)-4,5-difluoro-4,5-dichloro-1,3-dioxolane is used to produce the dioxole, A multi-plate distillation column may be used to separate the cis and trans isomers. Preferably, the cis isomer as well as 2,2-bis(perhaloalkyl)-4,4,5,5-tetrachloro-1,3-dioxolane and -4-fluoro-4,5,5-trichloro-1,3-dioxolane are recycled to the fluorination step.

The dioxole in turn may be used to prepare homopolymers and copolymers which possess advantageous properties such as chemical inertness to hydrogen fluoride, optical clarity and film-forming ability.

For example, the dioxoles may be copolymerized under standard polymerization conditions with tetrafluoroethylene to form crystalline copolymers suitable for use as a dielectric in electronic equipment. Preferably, in these applications the dioxole is employed in an amount of about 12 mole % or less.

Polymers having more than about 12% dioxole are more generally amorphous, and are soluble in various organic liquids, e.g., 1,1,2-trichloro-1,2,2-trifluoroethane. These polymers are useful in the production of chemically inert, stain and weather resistant coatings and finishes.

Further, the dioxoles may be reacted with vinylidene fluoride or tetrafluoroethylene to produce plastic and/or elastomeric terpolymers useful in the production of corrosion-resistant seals, gaskets or linings.

Finally, the dioxoles may be homopolymerized to produce amorphous resins suitable for use as transparent glazing materials and sight glasses in apparatuses employed in handling chemically corrosive materials.

In particular, the amorphous polymers are useful in the production of optical fiber cladding materials, e.g., in accordance with U.S. Pat. Nos. 4,530,569 and 4,754,009.

Various fluoropolymers have been proposed from time to time for this purpose, mainly because of their good performance under a variety of temperature and atmospheric conditions and resistance to many chemicals. A good polymeric cladding material for optical fibers should be completely amorphous because crystallites present in polymers would cause light scattering. Further, it should have a high glass transition temperature, Tg, especially if intended for use at high temperatures because above its Tg, it would lose some of its desirable physical properties; and, in particular, it would be unable to maintain good bonding to the fiber core. A desirable Tg would be above 85° C., preferably above 120° C.

As the amount of dioxole in the copolymer increases, the Tg also increases, although not necessarily in a linear fraction.

A homopolymer of dioxole appears to be amorphous and has a high Tg. However, dioxole is a much more expensive monomer than tetrafluoroethylene so that use of dioxole homopolymers, rather than of dioxole/tetrafluoroethylene copolymers, is economically much less attractive. Furthermore, the copolymers are easier to fabricate. The dipolymers have low refractive indices, which is a particularly desirable feature for optical fiber cladding. Furthermore, films of these copolymers are clear and transparent, compared with hazy or translucent films of crystalline polymers. For this reason, the amorphous copolymers of the present invention are suitable for such applications as, for example, windows for chemical reactors, especially for processes using or manufacturing hydrogen fluoride.

Amorphous terpolymers can be made by copolymerizing certain ethylenically unsaturated monomers with perfluoro-2,2-dimethyl-1,3-dioxole and tetrafluoroethylene. These include selected olefins, vinyl compounds, and perfluoromonomers. Typical olefins are, for example, ethylene, propylene, 1-butene, isobutylene, trifluoropropene, and trifluoroethylene. Vinyl monomers can be, for example, vinyl fluoride, vinylidene fluoride, and chlorotrifluoroethylene. Perfluoromonomers may be of different chemical types, for example, perfluoropropene, perfluoro(1,3-dioxole), perfluoro(alkyl vinyl ethers), methyl 3-[1-[difluoro(trifluoroethenyl)oxy]methyl]-1,2,2,2-tetrafluoroethoxy]-2,2,3,3-tetrafluoropropanoate

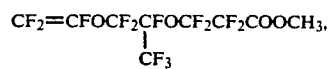

and 2-[1-[difluoro[(trifluoroethenyl)oxy]methyl]-1,2,2,2-tetrafluorooethoxy]-1,1,2,2-tetrafluoroethanesulfonyl fluoride

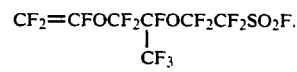

The proportion of dioxole in the amorphous terpolymers of this invention should preferably be at least 12 mole percent of the tetrafluoroethylene content, while the mole percent content of the third monomer should be the smallest of all three monomers. Outside these limits, either an amorphous terpolymer may not be obtained; or, if made, its maximum tensile modulus and strength may not be realized.

Copolymerization is carried out in the presence of a free radical generator, preferably at a slightly elevated temperature, for example, 55°–65° C. Well-agitated pressure equipment should be used.

In addition to tetrafluoroethylene, amorphous copolymers may be fabricated from the dioxole and chlorotrifluoroethylene; vinylidene fluoride; hexafluoropropylene; trifluoroethylene; perfluoro(alkyl vinyl ethers) of the formula $CF_2=CFOR_F$, where $R_F$ is a normal perfluoroalkyl radical having 1–3 carbon atoms; fluorovinyl ethers of the formula $CF_2=CFOQZ$, where Q is a perfluorinated alkylene radical containing 0–5 ether oxygen atoms, wherein the sum of the C and O atoms in Q is 2 to 10, and Z is a group selected from the class consisting of —CN, —COF, and —OCH$_3$, where R is a $C_{1-C4}$ alkyl; vinyl fluoride; and (perfluoroalkyl-)ethylene, $R_fCH=CH_2$, where $R_f$ is a $C_{1-C8}$ normal perfluoroalkyl radical.

The maximum preferred mole percentage of the co-monomer in the copolymers are as follows:
for tetrafluoroethylene, 35;
for chlorotrifluoroethylene, 30
for vinylidene fluoride, 20;
for hexafluoropropylene, 5;
for trifluoroethylene, 30;
for $CF_2=CFOR_F$, 30;
for $CF_2=CFOQZ$, 20;
for vinyl fluoride, 25; and
for $R_fCH=CH_2$, 10.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the preceding text and the following examples, all temperatures are set forth uncorrected in degrees Celsius and all parts and percentages are by weight, unless otherwise indicated. Amounts of compounds listed in the Tables are given in area %. C.T. represents contact time.

In the following examples, the numbers identifying the compounds in the tables are as follows:
D456 - 2,2-Bis(trifluoromethyl)-1,3-dioxolane
D436 - 2,2-Bis(trifluoromethyl)-4,5-dichloro-1,3-dioxolane
D436a - 2,2-Bis(trifluoromethyl)-4,4-dichloro-1,3-dioxolane
D426 - 2,2-Bis(trifluoromethyl)-4,4,5-trichloro-1,3-dioxolane
D416 - 2,2-Bis(trifluoromethyl)-4,4,5,5-tetrachloro-1,3-dioxolane
D417 - 2,2-Bis(trifluoromethyl)-4-fluoro-4,5,5-trichloro-1,3-dioxolane
D418a - 2,2-Bis(trifluoromethyl)-4,4-difluoro-5,5-dichloro-1,3-dioxolane
D418 - 2,2-Bis(trifluoromethyl)-4,5-dichloro-4,5-dichloro-1,3-dioxolane
D419 - 2,2-Bis(trifluoromethyl)-4,4,5-trifluoro-5-chloro-1,3-dioxolane.

EXAMPLES

General Procedure for Chlorination

The reactor (0.5 inch ID Inconel\ nickel alloy pipe) was charged with the designated amount of catalyst, sealed and placed into a sand bath. The bath was heated to 400° C., at which time nitrogen gas at a flow rate of 50 ml/minute was passed through the reactor to remove all traces of water. Chlorine gas at a flow rate of 25.7 cc/min was passed through the reactor and the temperature adjusted to the desired value. The flow of nitrogen gas was turned off and the flow of D456 started. The flow of chlorine and D456 were adjusted to give the desired molar ratio.

The reactor effluent was scrubbed with aqueous potassium hydroxide to remove Cl$_2$, HCl and HF and sampled on line by a HP 5890 gas chromatograph using a 5 foot Krytox\ perfluorinated polyether column. Conditions were 70° C. for 3 minutes followed by temperature programming to 180° C at a rate of 6° C./minute. Helium flow was 35 cc/minute.

General Procedure for Fluorination

The reactor (0.5 inch ID Inconel\ nickel alloy pipe) was charged with the designated amount of catalyst, sealed and placed into a sand bath. The bath was heated to 400° C., at which time nitrogen gas at a flow rate of 50 ml/minute was passed through the reactor to remove all traces of water. The temperature was lowered to 200° C., and HF and nitrogen gas (1:4 molar ratio) was passed through the reactor, and the nitrogen flow was decreased with time until neat HF was being passed through the reactor. At this point, the temperature is raised to 350° C. and maintained there for 15 to 30 minutes. The temperature is then decreased to the desired temperature, and the D416 flow is started. The flow of HF and D416 were adjusted to give the desired molar ratio.

The reactor effluent was scrubbed with aqueous potassium hydroxide to remove Cl$_2$, HCl and HF and sampled on line by a HP 5890 gas chromatograph using a 5 foot Krytox\ perfluorinated polyether column. Conditions were 70° C. for 3 minutes followed by temperature programming to 180° C. at a rate of 6° C./minute. Helium flow was 35 cc/minute.

EXAMPLE 1–16

Chlorination of 2,2-Bis(trifluoromethyl)-1,3-Dioxolane (D456)

CuCl$_2$/C 19.7 grams (30 cc)

| Exp | Temp | Cl$_2$/D456 | C.T. | D436 | D426 | D416 | Unk |
|---|---|---|---|---|---|---|---|
| 1 | 225 | 6/1 | 30 | 14 | 40 | 43 | 3 |
| 2 | 235 | 6/1 | 30 | 5 | 29 | 62 | 3 |
| 3 | 245 | 6/1 | 30 | 3 | 21 | 74 | 2 |
| 4 | 255 | 6/1 | 30 | 1 | 9 | 88 | 2 |
| 5 | 265 | 6/1 | 30 | 0 | 5 | 93 | 2 |
| 6 | 195 | 6/1 | 60 | 43 | 33 | 16 | 8 |
| 7 | 205 | 6/1 | 60 | 25 | 44 | 24 | 5 |
| 8 | 215 | 6/1 | 60 | 10 | 44 | 42 | 4 |
| 9 | 225 | 6/1 | 60 | 5 | 34 | 57 | 3 |
| 10 | 235 | 6/1 | 60 | 1 | 18 | 80 | 1 |
| 11 | 245 | 6/1 | 60 | 0 | 7 | 90 | 3 |
| 12 | 255 | 6/1 | 60 | 0 | 2 | 95 | 3 |
| 13 | 265 | 6/1 | 60 | 0 | 0 | 97 | 3 |
| 14 | 275 | 6/1 | 60 | 0 | 0 | 96 | 4 |
| 15 | 285 | 6/1 | 60 | 0 | 0 | 95 | 5 |

-continued

| Exp | Temp | Cl₂/D456 | C.T. | D436 | D426 | D416 | Unk |
|---|---|---|---|---|---|---|---|
| 16 | 285 | 4/1 | 60 | 0 | 1 | 95 | 4 |

The conversion of D456 to products was 100%, as shown in the Table.

EXAMPLES 17-23

Chlorination of 2,2-Bis(trifluoromethyl)-1,3-Dioxolane (D456)

CuCl₂/C 19.7 grams (30 cc)

| Exp | Temp | Cl₂/D456 | C.T. | D426 | D416 | D417 | Unk |
|---|---|---|---|---|---|---|---|
| 17 | 265 | 6/1 | 60 | 1 | 97 | 0 | 2 |
| 18 | 265 | 6/1 | 60 | 1 | 97 | 0 | 1 |
| 19 | 265 | 6/1 | 60 | 1 | 97 | 0 | 3 |
| 20 | 265 | 5/1 | 75 | 1 | 97 | 1 | 0 |
| 21 | 265 | 4/1 | 75 | 3 | 95 | 0 | 2 |
| 22 | 265 | 5/1 | 60 | 2 | 95 | 0 | 3 |
| 23 | 275 | 5/1 | 60 | 0 | 97 | 0 | 2 |

The conversion of D456 to products was 100%, as shown in the Table.

EXAMPLES 24-28

Chlorination of 2,2-Bis(trifluoromethyl)-1,3-Dioxolane (D456)

LaCl₃/C 4.25 grams (5 cc)

| Exp | Temp | Cl₂/D456 | C.T. | D456 | D436 | D426 | D416 | D417 | Unk |
|---|---|---|---|---|---|---|---|---|---|
| 24 | 200 | 6/1 | 10 | 3 | 74 | 12 | 10 | 0 | 1 |
| 25 | 225 | 6/1 | 10 | 4 | 64 | 11 | 18 | 0 | 3 |
| 26 | 250 | 6/1 | 10 | 1 | 43 | 9 | 43 | 1 | 2 |
| 27 | 275 | 6/1 | 10 | 0 | 22 | 6 | 67 | 1 | 4 |
| 28 | 300 | 6/1 | 10 | 0 | 9 | 3 | 72 | 3 | 13 |

EXAMPLES 29-32

Chlorination of 2,2-Bis(trifluoromethyl)-1,3-Dioxolane (D456)

SnCl₂/C 4.0 grams (5 cc)

| Exp | Temp | Cl₂/D456 | C.T. | D436 | D426 | D416 | D427 | D417 | Unk |
|---|---|---|---|---|---|---|---|---|---|
| 29 | 225 | 6/1 | 10 | 36 | 37 | 23 | 1 | 0 | 2 |
| 30 | 250 | 6/1 | 10 | 13 | 29 | 53 | 1 | 1 | 3 |
| 31 | 275 | 6/1 | 10 | 2 | 8 | 74 | 1 | 2 | 8 |
| 32 | 275 | 5/1 | 10 | 2 | 9 | 70 | 0 | 2 | 12 |

The conversion of D456 to products was 100%, as shown in the Table.

EXAMPLES 33-37

Chlorination of 2,2-Bis(trifluoromethyl)-1,3-Dioxolane (D456)

FeCl₃/C 3.4 grams (5 cc)

| Exp | Temp | Cl₂/D456 | C.T. | D456 | D436 | D426 | D416 | D427 | D417 | Unk |
|---|---|---|---|---|---|---|---|---|---|---|
| 33 | 200 | 6/1 | 10 | 11 | 36 | 2 | 8 | 4 | 0 | 39 |
| 34 | 150 | 6/1 | 10 | 36 | 51 | 1 | 0 | 3 | 0 | 9 |
| 35 | 200 | 6/1 | 1 | 67 | 21 | 1 | 1 | 2 | 1 | 7 |
| 36 | 250 | 6/1 | 1 | 37 | 25 | 1 | 6 | 3 | 0 | 28 |
| 37 | 250 | 4/1 | 1 | 42 | 19 | 1 | 5 | 2 | 0 | 31 |

EXAMPLES 38-41

Chlorination of 2,2-Bis(trifluoromethyl)-1,3-Dioxolane (D456)

ZnCl₂/C 3.8 grams (5 cc)

| Exp | Temp | Cl₂/D456 | C.T. | D456 | D436 | D426 | D416 | D417 | Unk |
|---|---|---|---|---|---|---|---|---|---|
| 38 | 200 | 6/1 | 10 | 27 | 62 | 5 | 4 | 0 | 2 |
| 39 | 225 | 6/1 | 10 | 15 | 70 | 10 | 4 | 0 | 1 |
| 40 | 250 | 6/1 | 10 | 7 | 66 | 15 | 11 | 0 | 1 |
| 41 | 275 | 6/1 | 10 | 1 | 28 | 13 | 50 | 2 | 6 |

EXAMPLES 42-51

Fluorination of 2,2-Bis(trifluoromethyl)-4,4,5,5-tetrachloro-1,3-Dioxolane

Cr₂O₃ 28.9 g (30 cc) −12+20 mesh

| Exp | Temp | HF/D416/HCl | C.T. | D419 | tD418 | cD418 | D418a | D427 | D416 | Unk |
|---|---|---|---|---|---|---|---|---|---|---|
| 42 | 175 | 2/1/0 | 60 | 2 | 74 | 18 | 0 | 4 | 0 | 1 |
| 43 | 200 | 2/1/0 | 60 | 37 | 10 | 3 | 36 | 10 | 1 | 0 |
| 44 | 165 | 2/1/0 | 60 | 19 | 37 | 9 | 13 | 20 | 1 | 1 |
| 45 | 175 | 2/1/0 | 60 | 15 | 62 | 16 | 2 | 5 | 0 | 0 |
| 46 | 175 | 3/1/0 | 45 | 3 | 77 | 19 | 0 | 0 | 0 | 1 |
| 47 | 175 | 3/1/4 | 45 | 13 | 66 | 18 | 1 | 2 | 0 | 0 |
| 48 | 175 | 4/1/4 | 40 | 4 | 75 | 20 | 0 | 2 | 0 | 0 |
| 49 | 175 | 5/1/4 | 35 | 3 | 75 | 20 | 0 | 1 | 0 | 1 |
| 50 | 175 | 5/1/4 | 40 | 3 | 75 | 20 | 0 | 1 | 0 | 1 |
| 51 | 175 | 5/1/4 | 40 | 4 | 74 | 20 | 0 | 1 | 0 | 1 | t = trans
c = cis

EXAMPLES 52-54

Fluorination of
2,2-Bis(trifluoromethyl)-4,4,5,5-tetrachloro-1,3-Dioxolane

CoCl$_2$/C 12.3 g (30 cc)

| Exp | Temp | HF/D416 | C.T. | tD418 | cD418 | D417 | Unk |
|---|---|---|---|---|---|---|---|
| 52 | 200 | 10/1/0 | 30 | 44 | 350 | 8 | 7 |
| 53 | 200 | 5/1/0 | 60 | 39 | 33 | 16 | 6 |
| 54 | 165 | 10/1/0 | 30 | 47 | 37 | 8 | 3 |

EXAMPLES 55-59

Fluorination of
2,2-Bis(trifluoromethyl)-4,4,5,5-tetrachloro-1,3-Dioxolane

Cr$_2$O$_3$ 14.4 g (15 cc) −12+20 mesh

| Exp | Temp | HF/D416 | C.T. | D419 | tD418 | cD418 | D417 | Unk |
|---|---|---|---|---|---|---|---|---|
| 55 | 200 | 3/1/0 | 30 | 1 | 72 | 22 | 7 | 5 |
| 56 | 200 | 3/1/0 | 30 | 0 | 71 | 26 | 0 | 3 |
| 57 | 210 | 3/1/0 | 30 | 1 | 73 | 24 | 0 | 2 |
| 58 | 220 | 3/1/0 | 30 | 1 | 72 | 24 | 0 | 3 |
| 59 | 230 | 3/1/0 | 30 | 1 | 73 | 23 | 1 | 2 |

COMPARATIVE EXAMPLES 60-68

Fluorination of
2,2-Bis(trifluoromethyl)-4,4,5,5-tetrachloro-1,3-Dioxolane

LaCl$_3$/C 4.25 g (5 cc)

| Exp | Temp | HF/D416 | C.T. | t418 | cD418 | D417 | D416 | Unk |
|---|---|---|---|---|---|---|---|---|
| 60 | 225 | 2/1/0 | 10 | 2 | 4 | 85 | 3 | 6 |
| 61 | 250 | 2/1/0 | 10 | 14 | 13 | 67 | 0 | 5 |
| 62 | 275 | 2/1/0 | 10 | 26 | 27 | 0 | 0 | 4 |
| 63 | 300 | 2/1/0 | 10 | 34 | 33 | 26 | 0 | 7 |
| 64 | 300 | 2/1/0 | 20 | 43 | 35 | 11 | 0 | 10 |
| 65 | 300 | 2/1/0 | 20 | 44 | 36 | 9 | 0 | 11 |
| 66 | 250 | 2/1/0 | 40 | 41 | 38 | 14 | 0 | 7 |
| 67 | 250 | 2/1/0 | 40 | 38 | 35 | 20 | 0 | 7 |
| 68 | 300 | 2/1/0 | 40 | 46 | 31 | 4 | 0 | 11 |

EXAMPLES 69-72

Fluorination of
2,2-Bis(trifluoromethyl)-4,4,5,5-tetrachloro-1,3-Dioxolane

FeCl$_3$/C 3.4 g (5 cc)

| Exp | Temp | HF/D416 | C.T. | tD418 | cD418 | D417 | D416 | Unk |
|---|---|---|---|---|---|---|---|---|
| 69 | 200 | 2/1/0 | 5 | 0 | 0 | 24 | 71 | 5 |
| 70 | 225 | 2/1/0 | 5 | 0 | 0 | 42 | 54 | 8 |
| 71 | 275 | 2/1/0 | 10 | 7 | 8 | 76 | 1 | 8 |
| 72 | 275 | 3/1/0 | 10 | 9 | 10 | 70 | 0 | 11 |

EXAMPLES 73-79

Fluorination of
2,2-Bis(trifluoromethyl)-4,4,5,5-tetrachloro-1,3-Dioxolane

NiCl$_2$/C 1.66 g (3 cc) ⅛-inch Pellets

| Exp | Temp | HF/D416 | C.T. | tD418 | cD418 | D417 | D416 | Unk |
|---|---|---|---|---|---|---|---|---|
| 73 | 200 | 2/1/0 | 5 | 0 | 0 | 5 | 91 | 4 |
| 74 | 220 | 2/1/0 | 5 | 0 | 0 | 7 | 88 | 5 |
| 75 | 240 | 2/1/0 | 5 | 0 | 0 | 13 | 80 | 7 |
| 76 | 260 | 2/1/0 | 5 | 0 | 0 | 31 | 61 | 6 |
| 77 | 280 | 2/1/0 | 5 | 1 | 2 | 45 | 39 | 10 |
| 78 | 280 | 4/1/0 | 5 | 5 | 4 | 66 | 10 | 13 |
| 79 | 325 | 4/1/0 | 5 | 8 | 7 | 34 | 2 | 48 |

EXAMPLES 80-83

Fluorination of
2,2-Bis(trifluoromethyl)-4,4,5,5-tetrachloro-1,3-Dioxolane

CuCl$_2$/C 19.7 g (30 cc)

| Exp | Temp | HF/D416 | C.T. | tD418 | cD418 | D417 | D416 | Unk |
|---|---|---|---|---|---|---|---|---|
| 80 | 200 | 3/1/0 | 30 | 2 | 2 | 66 | 13 | 16 |
| 81 | 200 | 3/1/0 | 30 | 6 | 5 | 73 | 3 | 13 |
| 82 | 250 | 3/1/0 | 30 | 4 | 4 | 85 | 0 | 5 |
| 83 | 250 | 3/1/0 | 30 | 4 | 4 | 85 | 0 | 6 |

EXAMPLES 84-85

Fluorination of
2,2-Bis(trifluoromethyl)-4,4,5,5-tetrachloro-1,3-Dioxolane

SnCl$_2$/C 4.0 g (5 cc)

| Exp | Temp | HF/D416 | C.T. | tD418 | cD418 | D417 | D416 | Unk |
|---|---|---|---|---|---|---|---|---|
| 84 | 275 | 2/1/0 | 10 | 9 | 10 | 74 | 2 | 5 |
| 85 | 275 | 2/1/0 | 20 | 19 | 17 | 60 | 0 | 4 |

EXAMPLES 86-87

Fluorination of
2,2-Bis(trifluoromethyl)-4,4,5,5-tetrachloro-1,3-Dioxolane

ZnCl$_2$/C 3.8 g (5 cc)

| Exp | Temp | HF/D416 | C.T. | tD418 | cD418 | D417 | D416 | Unk |
|---|---|---|---|---|---|---|---|---|
| 86 | 300 | 2/1/0 | 10 | 6 | 7 | 73 | 10 | 4 |
| 87 | 250 | 2/1/0 | 10 | 1 | 2 | 53 | 44 | 1 |

EXAMPLE 88

Examples Describing the Rearrangement of Cis-D418 to Trans-D418

A mixture of 150 g D-418 (65.5% trans isomer), 6.0 g antimony pentachloride, and 20 g anhydrous hydrogen fluoride was heated at 100° for one hour and 135° for five hours. The reaction mixture was added to ice/ice water and the lower layer washed with 400 ml ice water to give 139.3 g of product. Analysis showed this product to contain 1.3 g D-419 and 138.0 g D-418 (79.8% trans isomer). Thus the amount of trans D-418 rose from 98.3 g to 110.1 g, while the amount of cis isomer fell from 51.7 to 27.9 g.

A mixture of 40.5 g D-418 (53.5% trans isomer), 4.0 g antimony pentachloride, and 20 g anhydrous hydrogen fluoride was heated at 100 for one hour and 135° for four hours. The reaction mixture was added to ice/ice water and the lower layer separated to give 35.4 g of product containing 26.7 g trans D-418 and 8.5 g cis D-418 (78.4% trans isomer). Thus the amount of trans D-418 rose from 21.7 g to 26.7 g, while the amount of cis D-418 declined from 18.8 g to 8.5. g.

EXAMPLE 89

Variation in Yield of Perfluoro-2,2-bis-trifluoromethyl-1,3-dioxole (PDD) with cis/trans bis-2,2-trifluoromethyl-4,5-dichloro-4,5-difluoro-1,3-dioxolane (D418)

A mixture of 24.9 g magnesium turnings and 395 ml tetrahydrofuran was heated 60°. After addition of 2.75 ml, 1,2-dibromoethane approximately 4.5 g bis-2,2-trifluoromethyl-4,5-dichloro-4,5-difluoro-1,3-dioxolane (D418) was added. The reaction mixture was cooled to 35°-40° and a total of 133 g cis/trans D418 added. After stirring for 15 minutes, the mixture was distilled until the pot temperature reached 70°. The distillate boiling to 45° was washed with 100 ml of ice water. Gas chromatographic analysis of the lower layer showed it to be greater than 99% PDD.

| Percent Trans Isomer in Starting D418 | Yield of PDD Percent |
| --- | --- |
| 97.7 | 60.7 |
| 83.6 | 51.7 |
| 64.7 | 40.2 |

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A process for the production of a halogenated 2,2-bis(perhaloalkyl)-1,3-dioxolane of the formula

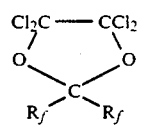

wherein each $R_f$ independently is perhaloalkyl in which the alpha carbon atom is substituted by at least one fluorine atom, comprising reacting under chlorination conditions a 2,2-bis(perhaloalkyl)-1,3-dioxolane and a source of chlorine in the presence of a catalyst which is at least one of any soluble compound of La, Ni, Sn, Zn, Fe, Co or Cu.

2. A process according to claim 1, wherein the catalyst is in the form of a supported metal chloride.

3. A process according to claim 2, wherein the catalyst is in the form of metal chloride supported on carbon.

4. A process according to claim 1, wherein the catalyst is $CuCl_2$ supported on carbon.

5. A process according to claim 1, wherein the temperature is about 250°-300° C., the ratio of chlorine to 2,2-bis(perhaloalkyl)-1,3-dioxolane is about 4:1-10:1, the reaction time is about 1-120 sec, and the reaction pressure is about 1-20 atm.

6. A process according to claim 1, wherein $R_f$ is $CF_3$.

7. A process for the production of a halogenated 2,2-bis(perhaloalkyl)-1,3-dioxolane of the formula

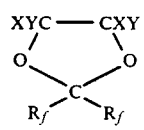

wherein X is Cl and each Y is independently Cl or F and at least one Y is F, and wherein each $R_f$ independently is perhaloalkyl in which the alpha carbon atom is substituted by at least one fluorine atom, comprising reacting. under fluorination conditions, 2,2-bis(perhaloalkyl)-4,4,5,5,-tetrachloro-1,3-dioxolane and hydrogen fluoride in the presence of a catalyst which is at least one of La, Ni, Sn, Zn, Fe, Co, Cu, or a member of the group consisting of the oxyhalide, halide, pseudohalide, nitrate, sulfate or organic salt of Cr.

8. In a process for the production of a halogenated 2,2-bis(perhaloalkyl)-1,3-dioxolane comprising (a) chlorinating 2,2-bis(perhaloalkyl)-1,3-dioxolane to produce a compound of the formula

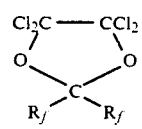

and (b) fluorinating the product compound of (a) to produce a compound of the formula

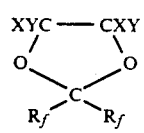

wherein X is Cl and Y is Cl or F, at least one Y being F, and wherein each $R_f$ independently is perhaloalkyl in which the alpha carbon atom is substituted by at least one fluorine atom, the improvement comprising conducting the chlorination of (a) in the presence of a catalyst which is at least one of any soluble compound of La, Ni, Sn, Zn, Fe, Co or Cu.

9. In a process for the production of 2,2-bis(perhaloalkyl)-1,3-dioxole of the formula

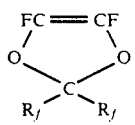

wherein each $R_f$ independently is perhaloalkyl in which the alpha carbon atom is substituted by at least one fluorine atom, comprising chlorinating a corresponding 2-bis(perhaloalkyl)-1,3-dioxolane, fluorinating the product and subsequently dehalogenating to form the 1,3-dioxole, the improvement comprising conducting the chlorination in the presence of a catalyst which is at least one of any soluble compound of La, Ni, Sn, Zn, Fe, Co or Cu.

10. A process according to claim 9, wherein the improvement further comprising conducting the fluorination in the presence of a catalyst which is at least one of Cr, La, Ni, Sn, Zn, Fe, Co or Cu.

11. A process according to claim 9, wherein the improvement further comprises, prior to dehalogenating, separating trans-2,2-bis(perhaloalkyl)-4,5-difluoro-4,5-dichloro-1,3-dioxolane and dehalogenating substantially only said isomer.

12. A process according to claim 10, wherein the improvement further comprises, prior to dehalogenating, separating trans-2,2-bis(perhaloalkyl)-4,5-difluoro-4,5-dichloro-1,3-dioxolane and dehalogenating substantially only said isomer.

13. The process according to claim 9 wherein fluorination is conducted in the presence of $Cr_2O_3$ and the product is at least 65% trans isomer.

14. In a process for the production of 2,2-bis(perhaloalkyl)-1,3-dioxole of the formula

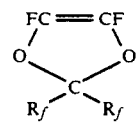

wherein each $R_f$ independently is perhaloalkyl in which the alpha carbon atom is substituted by at least one fluorine atom, comprising chlorinating a corresponding 2,2-bis(perhaloalkyl)-1,3-dioxolane, fluorinating the product and subsequently dehalogenating to form the 1,3-dioxole, the improvement comprising conducting the fluorination using hydrogen fluoride in the presence of a catalyst which is at least one of La, Ni, Sn, Zn, Fe, Co, Cu, or a member of the group consisting of the oxyhalide, halide, pseudohalide, nitrate, sulfate or organic salt of Cr.

* * * * *